(12) United States Patent
Nagai et al.

(10) Patent No.: US 7,098,186 B2
(45) Date of Patent: Aug. 29, 2006

(54) DEPSIPEPTIDE COMPOUND

(75) Inventors: Koji Nagai, Itabashi-ku (JP); Masatoshi Taniguchi, Tsukuba (JP); Nobuaki Shindo, Tsukuba (JP); Yoh Terada, Tsukuba (JP); Masamichi Mori, Tsukuba (JP); Nobuaki Amino, Tsukuba (JP); Ken-ichi Suzumura, Tsukuba (JP); Isao Takahashi, Itabashi-ku (JP); Mitsuo Amase, Itabashi-ku (JP)

(73) Assignee: Astellas Pharma INC, Tokyo (JP)

( * ) Notice: Subject to any disclaimer, the term of this patent is extended or adjusted under 35 U.S.C. 154(b) by 0 days.

(21) Appl. No.: 10/525,717

(22) PCT Filed: Aug. 28, 2003

(86) PCT No.: PCT/JP03/10957

§ 371 (c)(1), (2), (4) Date: Feb. 25, 2005

(87) PCT Pub. No.: WO2004/020460

PCT Pub. Date: Nov. 3, 2004

(65) Prior Publication Data

US 2005/0209134 A1    Sep. 22, 2005

(30) Foreign Application Priority Data

Aug. 30, 2002    (JP) .............................. 2002-255141

(51) Int. Cl.
*A61K 38/12*    (2006.01)
*C07K 2/00*    (2006.01)

(52) U.S. Cl. ............................ 514/11; 530/300; 514/2; 514/9

(58) Field of Classification Search ..................... None
See application file for complete search history.

(56) References Cited

U.S. PATENT DOCUMENTS 6,670,326 B1    12/2003   Nagai et al.
2003/0082054 A1    5/2003   Grylls et al.

FOREIGN PATENT DOCUMENTS

JP    2001-348340 A    12/2001
WO    WO 00-42062 A1    7/2000

OTHER PUBLICATIONS

D. Voet and J.G. Voet. Biochemistry, 2nd Edition.(1995), p. 58.*

* cited by examiner

*Primary Examiner*—Bruce R. Campell
*Assistant Examiner*—Andrew D. Kosar
(74) *Attorney, Agent, or Firm*—Sughrue Mion, PLLC (57) ABSTRACT

The present invention relates to a novel compound which is useful as an agent for prevention and treatment of diseases associated with HDAC, in particular, tumor or cell proliferative diseases. The depsipeptide compound or its pharmaceutically acceptable salt of the present invention has a good HDAC inhibitory activity and an inhibitory activity of cell proliferation against human cancer cells and, therefore, is useful in treatment and improvement of diseases and pathogenic conditions associated with histone acetylation, in particular, tumor or cell proliferative diseases.

4 Claims, 4 Drawing Sheets

DEPSIPEPTIDE COMPOUND

TECHNICAL FIELD

The present invention relates to a novel depsipeptide compound which is useful as a medicament, in particular a histone deacetylase inhibitor and an antitumor agent.

BACKGROUND ART

It is known that histone acetylation is controlled by the balance of histone acetyltransferase (HAT) and histone deacetylase (HDAC). Recently some HATs and HDACs were identified and reported to play an important role in the regulation of gene expression (Ogryzko, V. V. et al., *Cell* 87, 953–959, 1996, Brown, C. E. et al., *Trends Biochem. Sci.* 25(1), 15–19, 2000, Grozinger, C. M. et al., *Proc. Natl. Acad. Sci. USA*, 96, 4868–4873, 1999).

On the other hand, it has been known that butyric acid having various functions such as cell cycle arrest, morphological normalization of transformed cells and induction of differentiation induces accumulation of a highly acetylated histones in cells and has an HDAC inhibitory activity (Counsens, L. S. et al., *J. Biol. Chem.* 254, 1716–1723, 1979). In addition, it was found out that Trichostatin A (TSA) which is a microorganism metabolite shows cell cycle arrest and induction of differentiation (Yoshida, M., et al., *Cancer Res.* 47, 3688–3691, 1987, Yoshida, M. et al., *Exp. Cell Res.* 177, 122–131, 1988) and induces apoptosis. TSA induces accumulation of a highly acetylated histones in cells, and from the study using partially purified HDAC, it was demonstrated that TSA is a strong HDAC inhibitor (Yoshida, M., et al., *J. Biol. Chem.* 265, 17174–17179, 1990).

The HDAC inhibitor has functions such as cell cycle arrest, morphological normalization of transformed cells, induction of differentiation, induction of apoptosis and inhibition of angiogenesis, therefore, the effect as an antitumor agent has been expected (Marks, P. A. et al., *J. Natl. Cancer Inst.*, 92, 1210–1216 2000, Kim, M. S. et al., *Nature Med.*, 7, 437–443, 2001). Other than this, various applications have been attempted, for example, for an agent for treatment and improvement of cell proliferative diseases such as infectious diseases, autoimmune diseases and dermatologic diseases (Darkin-Rattray, S. J. et al., *Proc. Natl. Acad. Sci. USA*, 93, 13143–13147, 1996), an agent for prevention and treatment of progressive neurodegenerative diseases such as Huntington's disease (Steffan, J. S. et al., *Nature*, 413, 739–743, 2001), enhancement of the expression of an introduced gene (Chen, W. Y. et al., *Proc. Natl. Acad. Sci. USA*, 94, 5798–5803, 1997) and the like, and it is expected to become an effective medicament.

In recent years, depsipeptide compounds derived from the culture broth of microorganisms having an HDAC inhibitory activity, for example, FK228 (see Non-Patent Reference 1) and the compounds A, B and C represented by the following formulae (see Patent References 1 and 2) have been reported. These compounds have a good HDAC inhibitory activity and are expected as a new type of antitumor agent.

Compound A

Compound B

Compound C

However, even at present, development and production of a medicament whose intensity of activity, stability, pharmacokinetics, toxicity and the like and further improved has been awaited anxiously.

[Non-Patent Document 1] Nakajima, H. et al., "*Experimental Cell Research*", Vol. 241, 126–133, 1998

[Patent Document 1] International Patent WO 00/42062

[Patent Document 2] JP-A-2001-348340

DISCLOSURE OF THE INVENTION

As a result of intensive studies on natural compounds produced by many microorganisms, the inventors of the present invention have found out a microorganism of new species Q71576 strain belonging to the genus *Pseudomonas*, and isolated novel depsipeptide compounds (the foregoing compounds A, B and C) having an excellent cell proliferation inhibitory activity against human cancer cells from the culture. Additionally, they found out that these compounds have an excellent HDAC inhibitory activity, and filed patent application in advance (see the foregoing Patent References 1 and 2).

The inventors of the present invention carried out additional intensive studies on culturing conditions, purification conditions and the like for further isolating a minor component in the culture mixture of the microorganism Q71576 strain and succeeded in isolating a novel analogous compound having an excellent HDAC inhibitory activity and inhibitory activity of cell proliferation against human cancer cells, thereby accomplishing the present invention.

Accordingly, the present invention relates to a depsipeptide compound represented by the following formula (I) (abbreviated as compound Q) or a depsipeptide compound represented by the following formula (II) (abbreviated as compound R), or a pharmaceutically acceptable salt thereof, preferably, an isomer of a depsipeptide compound having the planar structural formula represented by the following formula (I) and having an optical rotation $[\alpha]^{25}_D$ of −349.3 degree (c 0.05, methanol solvent) or an isomer of a depsipeptide compound having the planar structural formula represented by the following formula (II) and having an optical rotation $[\alpha]^{25}_D$ of −65.3 degree (c 0.20, methanol solvent), or a pharmaceutically acceptable salt thereof, which is useful as an HDAC inhibitor and an antitumor agent. It should be noted that the optical rotation $[\alpha]^{25}_D$ can vary to some extent according to the measurement condition due to the nature of data, therefore, the numerical values should not be construed strictly in identification of the isomers.

Additionally, the present invention relates to a pharmaceutical composition, particularly an antitumor agent comprising the depsipeptide compound represented by the foregoing formula (I) or (II), or the pharmaceutically acceptable salt thereof and a pharmaceutically acceptable carrier.

Further, the present invention comprises a use of the depsipeptide compound represented by the formula (I) or (II), or the pharmaceutically acceptable salt thereof for the manufacture of a medicament which is an antitumor agent, and a method for treatment of a patient suffering from cancer comprising administering an effective amount of the depsipeptide compound represented by the foregoing formula (I) or (II), or the pharmaceutically acceptable salt thereof to the patient.

The present invention will be described in detail in below.

The depsipeptide compound of the present invention or the pharmaceutically acceptable salt thereof can be obtained by culturing a bacterium producing the compound, which belongs to the genus *Pseudomonas* in a nutrient medium and from the culture of the accumulated compound by the usual method. As the microorganism to be used in the production method of the compound, any microorganism can be used as long as it belongs to the genus *Pseudomonas* and has the ability to produce the compound. As such a microorganism, a bacterial strain, *Pseudomonas* sp. Q71576, belonging to the genus *Pseudomonas* and isolated from a soil sample collected at Mochizuki-cho, Kitasaku-gun, Nagano Prefecture, for example, can be used. The bacteriological property of this strain is as described in WO 00/42062. Incidentally, the strain has been internationally deposited as the deposition number, FERM BP-6944 (deposited on Jan. 8, 1999) as *Pseudomonas* sp. Q71576 in International Patent Organism Depositary, National Institute of Advanced Industrial Science and Technology. Also, since microorganisms are apt to cause artificial or spontaneous mutation, the *Pseudomonas* sp. Q71576 strain used in the present invention includes not only microorganisms isolated from the nature but also those which are artificially mutated by ultraviolet rays, X rays, a chemical agent or the like and their spontaneous mutants.

(Production Method)

The compound of the present invention can be obtained by culturing a microorganism which belongs to the genus *Pseudomonas* and has the ability to produce the compound of the present invention. The culturing is carried out in accordance with a general culturing method of microorganisms.

The medium to be used in the culturing may be any medium as long as it contains nutrient sources utilized by *Pseudomonas* sp. Q71576 strain. A synthetic medium, a semi-synthetic medium or a natural medium is used. Generally known materials can be used as the nutrients to be added to the medium. With regard to the medium composition, D-glucose, D-mannose, D-fructose, inositol, D-mannitol, D-galactose, trehalose, xanthine, starch, glucose, dextrin, glycerol, plant oil and the like can be cited as examples of the carbon source. As the nitrogen source, meat extract, peptone, gluten meal, cottonseed meal, soybean powder, peanut powder, fish meal, corn steep liquor, dry yeast, yeast extract, ammonium chloride, ammonium sulfate, ammonium nitrate, uric acid and other organic and inorganic nitrogen sources can be used. Also, sulfate, nitrate, carbonate, phosphate and the like of sodium, potassium, magnesium, calcium, zinc, iron, cobalt and the like are added as metal salts, if necessary. Additionally, a production accelerating compound or an antifoaming agent such as methionine, cysteine, cystine, thiosulfate, methyl oleate, lard oil, silicon oil and surfactant can also be added, if necessary.

With regard to the culture condition, culturing under an aerobic condition is generally advantageous, and the culturing is carried out at the temperature of 3 to 32° C., preferably from approximately 20 to 28° C. Good results are obtained when the medium pH is adjusted to approximately from 4.5 to 9, preferably from about 5 to 7.5. The culturing period is optionally decided in accordance with the composition of the medium and temperature condition, but is generally from about 1 to 10 days, preferably from about 2 to 7 days.

In order to isolate the objective compound of the present invention from the culture, techniques usually used for extraction and purification of metabolites produced by microorganisms can be appropriately employed. For example, the objective compound among compounds in the culture is extracted by adding an organic solvent such as ethyl acetate which does not mix with water directly to the culture or to a culture obtained by centrifugation or by filtration after adding a filter aid to the culture mixture. The objective compound can also be extracted by allowing the culture to contact with an appropriate carrier, thereby effecting adsorption of the produced compound in the filtrate to the carrier, and then eluting the compound with an appropriate solvent. For example, the compound is adsorbed by allowing it to contact with a porous adsorption resin such as Amberlite™ (trade name) XAD-2, Diaion™ (trade name, hereinafter same as above) HP-20, Diaion™ CHP-20 or Diaion™ SP-900. Next, the compound is eluted using an organic solvent such as methanol, ethanol, acetone, butanol, acetonitrile or chloroform, alone or as a mixture, or a mixed solution of the solvent with water. In some cases, a fraction containing the compound can be efficiently obtained by increasing the mixing ratio of the organic solvent from a low concentration to a high concentration stepwise or continuously. When extracted with an organic solvent such as ethyl acetate or chloroform, the compound is extracted by adding such solvent to the culture filtrate and thoroughly shaking the mixture. Thereafter, the fraction containing the compound thus obtained using each of the above procedures can be separated and purified with higher purity by using a usually used method such as a column chromatography which uses silica gel, ODS or the like, a centrifugal liquid-liquid partition chromatography or a high performance liquid chromatography (HPLC) which uses ODS or recrystallization.

Examples of the pharmaceutically acceptable salt of the depsipeptide compound of the present invention include a salt with an inorganic or organic base, and specific examples include salts with inorganic bases such as sodium, potassium, magnesium, calcium and aluminum, organic bases such as methylamine, ethylamine, ethanolamine, lysine and ornithine, and complex salts with such as iron, and the like.

Also, since the compound of the present invention has an asymmetric carbon atom and a double bond, stereoisomers (racemic bodies, optical isomers, diastereomers and the like) and geometrical isomers (cis-forms or trans-forms) are present based on this. Consequently, the compound of the present invention includes mixtures or isolated products of these stereoisomers or geometrical isomers.

Furthermore, hydrates or various solvates of the compound and polymorphism of the compound are also included in the present invention.

The production method and method for use of the pharmaceutical composition which comprises the compound of the present invention as an active ingredient are described in detail in the following.

The pharmaceutical composition which comprises one or more of a depsipeptide compound of the present invention or a pharmaceutically acceptable salt thereof as the active ingredient is prepared into tablets, powders, fine subtilaes, granules, capsules, pills, solutions, injections, suppositories, ointments, pathces and the like using generally used pharmaceutical carriers, excipients and other additives and administered orally or parenterally.

With regard to clinical dose of the compound of the present invention to human, in the case of a common oral administration, a dose per day and per body surface area is appropriately, about 1 to 10,000 mg/m$^2$, preferably 10 to 5,000 mg/m$^2$, which is administered once or divided into 2 to 4 times. In the case of intravenous administration, a dose per day and per body surface area is, about 0.1 to 1,000 mg/m$^2$, which is divided into 1 to plural times per day. The dose is appropriately decided by taking into consideration of symptoms, age, sex and the like.

The solid composition for use in the oral administration according to the present invention is used in the form of tablets, powders, granules and the like. In such a solid composition, one or more active compounds are mixed with at least one inert diluent such as lactose, mannitol, glucose, hydroxypropylcellulose, microcrystalline cellulose, starch, polyvinyl pyrrolidone or magnesium aluminometasilicate. In accordance with the usual method, the composition may contain other additives than an inert diluent, for example, a lubricant such as magnesium stearate, a disintegrating agent such as calcium cellulose glycolate, a stabilizer and a solubilization assisting agent. If necessary, tablets or pills may be coated with a sugar such as sucrose, gelatin, hydroxypropylcellulose, hydroxypropylmethylcellulose phthalate or with a film of a gastric or enteric compound.

The liquid composition for oral administration includes pharmaceutically acceptable emulsions, solutions, suspensions, syrups, elixirs and the like and contains a generally used inert diluent such as purified water or ethyl alcohol. In addition to the inert diluent, the composition may also contain an auxiliary agent such as a solubilization assisting agent, moistening agent or suspending agent, as well as a sweetener, flavoring, aromatic or antiseptic.

The injections for parenteral administration include aseptic aqueous or non-aqueous solutions, suspensions and emulsions. Examples of the diluent for use in the aqueous solutions and suspensions include distilled water for injection use and physiological saline. Examples of the diluent for use in the non-aqueous solutions and suspensions include plant oils such as propylene glycol, polyethylene glycol and olive oil, alcohols such as ethyl alcohol, polysorbate 80 (trade name) and the like. Such a composition may further contain an additives such as a tonicity agent, antiseptic, moistening agent, emulsifying agent, dispersing agent, stabilizer or solubilization assisting agent. These compositions are sterilized by, for example, filtration through a bacteria retaining filter, blending of a germicide or irradiation. Alternatively, they may be used by firstly making into sterile solid compositions and then dissolving them in sterile water or a sterile solvent for injection use prior to their use.

If solubility of the compound of the present invention is low, its solubilization treatment may be carried out. The solubilization treatment can be performed by a generally known method which can be applied to pharmaceutical preparations, such as a method in which a surfactant (polyoxyethylene hydrogenated castor oil, a polyoxyethylene sorbitan higher fatty acid ester, a polyoxyethylene polyoxypropylene glycol, a sucrose fatty acid ester or the like) is added or a method in which a solid dispersion of the drug is formed with a solubilizing agent such as a polymer (a water-soluble polymer such as hydroxypropylmethylcellulose (HPMC), polyvinyl pyrrolidone (PVP) or polyethylene glycol (PEG), or an enteric polymer such as carboxymethylethylcellulose (CMEC), hydroxypropylmethylcellulose phthalate (HPMCP) or a methyl methacrylate-methacrylic acid copolymer (Eudragit L, S, trade name; by Rohm & Haas Co.)). If necessary, a method to form a soluble salt or a method to form an inclusion compound using cyclodextrin or the like can also be employed. The means for performing solubilization can be appropriately changed according to the objective agent [see "Recent Formulation Techniques and their Application I", Isamu Utsumi et al., *Medical Journal* 157–159 (1983) and "Pharmacy Monograph No. 1, Bioavailability", Koji Nagai et al., Soft Science Co., 78–82 (1988)].

BEST MODE FOR CARRYING OUT THE INVENTION

The present invention will be specifically explained in the following with reference to the Examples, however, the present invention is not limited thereto.

EXAMPLE 1

To a 500 ml Erlenmeyer flask, 100 ml of medium (pH 7.0) containing 10 g of glucose, 20 g of potato starch, 5 g of polypeptone, 5 g of yeast extract, 4 g of calcium carbonate and 1 L of distilled water was dispensed and sterilized at 120° C. for 20 minutes. Cells of *Pseudomonas* sp. Q71576 strain well grown in Bennett's agar medium were scratched off, inoculated into the medium and cultured at 28° C. for 3 days on a shaker under a condition of 200 rotation/min. to be used as the seed culture. Next, each 100 ml of medium (pH 5.0) containing 40 g of mannitol, 5 g of polypeptone, 5 g of meat extract, 2 g of magnesium sulfate heptahydrate, 0.5 g of L-cysteine hydrochloride hydrate and 1 L of tap water was dispensed into a 500 ml Erlenmeyer flask and sterilized at 120° C. for 20 minutes. A 2-ml portion of the foregoing seed culture was inoculated into the each of the medium and cultured at 24° C. for 3 days on a shaker under a condition of 220 rotation/min.

Centrifugation of 1 L of the thus culture at 6,000 rpm for 10 minutes was carried out. The supernatant was adjusted with 1 M hydrochloric acid to become pH of 3.0, extracted with ethyl acetate, dehydrated by adding anhydrous sodium sulfate and concentrated to be dryness under a reduced pressure. The oily crude extract was dissolved in methanol and repeatedly applied to HPLC (flow rate of 9 ml/min) using STR-PREP-ODS-M (20×250 mm) and acetonitrile/water (30/70), thus fraction 1 with a retention time of 28 to 36 minutes was obtained. The fraction 1 was concentrated to be dryness under a reduced pressure, dissolved in methanol and HPLC (flow rate of 9 ml/min) was carried out using COSMOSIL (20×250 mm) and acetonitrile/0.25% trifluoroacetic acid (40/60), thus fraction 2 of the peak with a retention time of 15.2 minutes and fraction 3 of the peak with a retention time of 16.5 minutes were obtained. By concentrating the fraction 2 to be dryness, 5.6 mg of compound Q was obtained, and by concentrating the fraction 3 to be dryness, 11.8 mg of compound R was obtained.

EXAMPLE 2

To a 500 ml Erlenmeyer flask, 100 ml of medium (pH 7.0) containing 10 g of glucose, 20 g of potato starch, 5 g of polypeptone, 5 g of yeast extract, 4 g of calcium carbonate and 1 L of distilled water was dispensed and sterilized at 120° C. for 20 minutes. Cells of *Pseudomonas* sp. Q71576 strain well grown in Bennett's agar medium were scratched off, inoculated into the medium and cultured at 28° C. for 3 days on a shaker under a condition of 200 rotation/min to be used as the primary seed culture. Next, 500 ml of the same medium as above was dispensed into a 3 L Erlenmeyer flask and sterilized at 120° C. for 20 minutes. The primary seed culture broth was inoculated into the medium at a concentration of 2% and cultured at 28° C. for 3 days on a shaker under a condition of 200 rotation/min to be used as the secondary seed culture. Then for the main culture, 200 L of medium (pH 5.0) containing 50 g of mannitol, 5 g of polypeptone, 5 g of meat extract, 2 g of magnesium sulfate heptahydrate, 0.5 g of L-cysteine, 0.5 g of L(–)-proline and 1 L of tap water was dispensed into a 300 L jar fermenter and sterilized at 120° C. for 20 minutes. The secondary seed culture was inoculated into the medium at a concentration of 1% and cultured at 20° C. for 7 days under a condition of 40 rotation/min and 200 L/min aeration rate.

After adjusting 200 L of the thus obtained culture with sulfuric acid to be pH 3.0, the culture was separated into cells and supernatant by a Sharples centrifuge. The supernatant was allowed to be passed through a column which has outer diameter of 18 cm and height of 150 cm packed with 20 L of Diaion™, HP-20 (Mitsubishi Chemical Co.) and the objective compound and the like were adsorbed thereto. Subsequently, the column was washed with 50 L of tap water, then washed with 40 L of 30% methanol/water, followed by 100 L of 30% acetone/water, and finally the objective compound was eluted with 60 L of methanol. To the eluted solution, 5 L of distilled water was added and concentrated under a reduced pressure to remove methanol. An equal amount of ethyl acetate was added thereto, and ethyl acetate extraction was performed at pH 3.0 for three times. After carrying out dehydration by adding anhydrous sodium sulfate to the extracted solution of ethyl acetate, concentration was performed to be dryness under a reduced pressure, whereby a crude purified substance containing the objective compound was obtained.

By adding 21.5 g of the thus obtained crude purified substance repeatedly to HPLC (flow rate of 8 ml/min), using YMC PACK Pro C18 20×250 mm (YMC) and acetonitrile/water (40/60), thus fraction 1 with a retention time of 18.0 to 19.8 minutes was obtained. The fraction 1 was concentrated until it became an aqueous solution, and subjected to freeze-drying. Then, it was repeatedly applied to HPLC (flow rate of 10 ml/min) using YMC PACK Pro C18 20×250 mm (YMC) and methanol/water (60/40), thus fraction 2 (retention time of 17.6 minutes) and fraction 3 (retention time of 21.2 minutes) were obtained. The fraction 2 was concentrated until it became an aqueous solution and subjected to freeze-drying, whereby 80 mg of compound Q was obtained. The fraction 3 was concentrated until it became an aqueous solution, subjected to freeze-drying, and recrystallized with ethanol, whereby 287 mg of compound R was obtained.

Physicochemical Property of the Compound of the Present Invention

Figure 1:
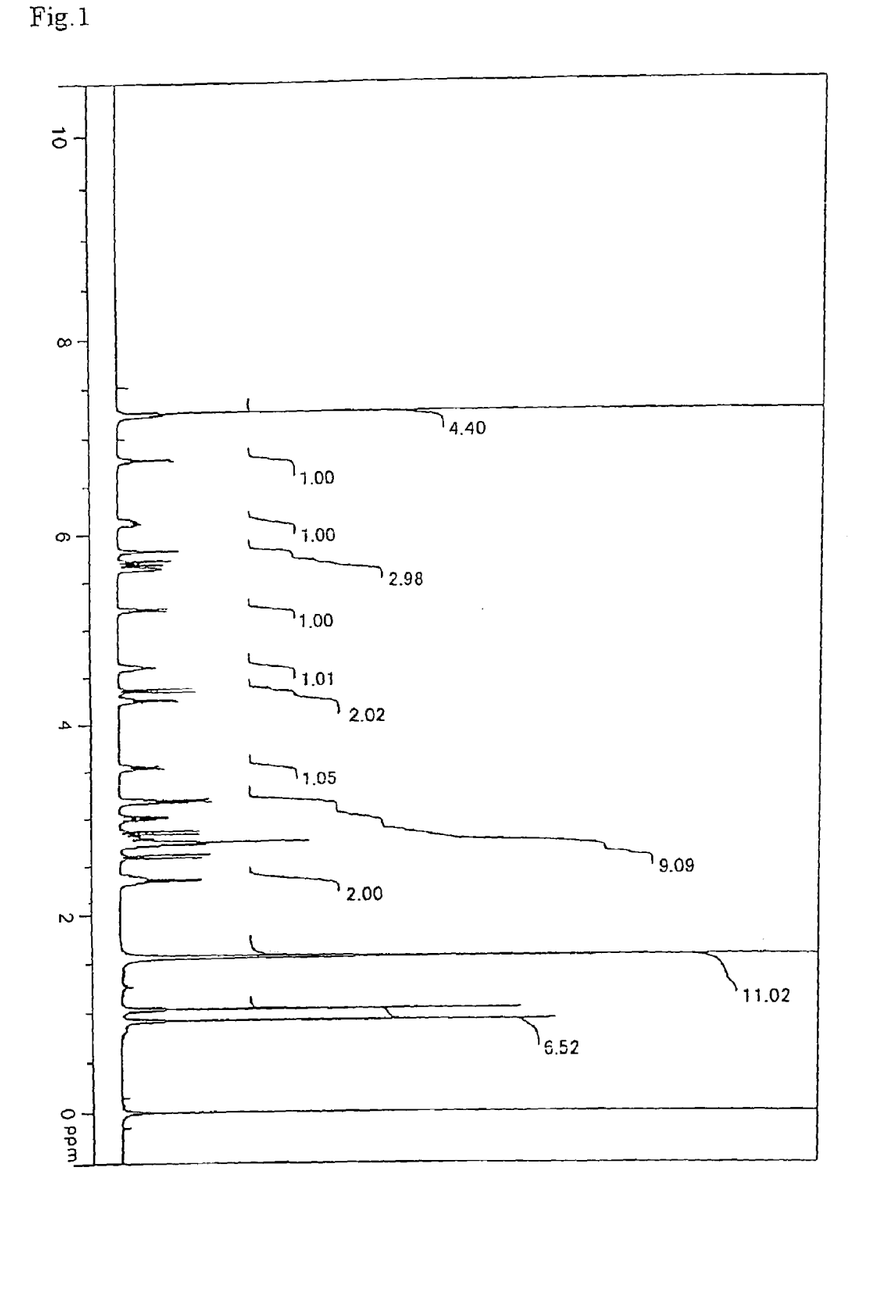
FIG. 1 shows the $^1$H-NMR spectrum of the compound Q.
Figure 2:
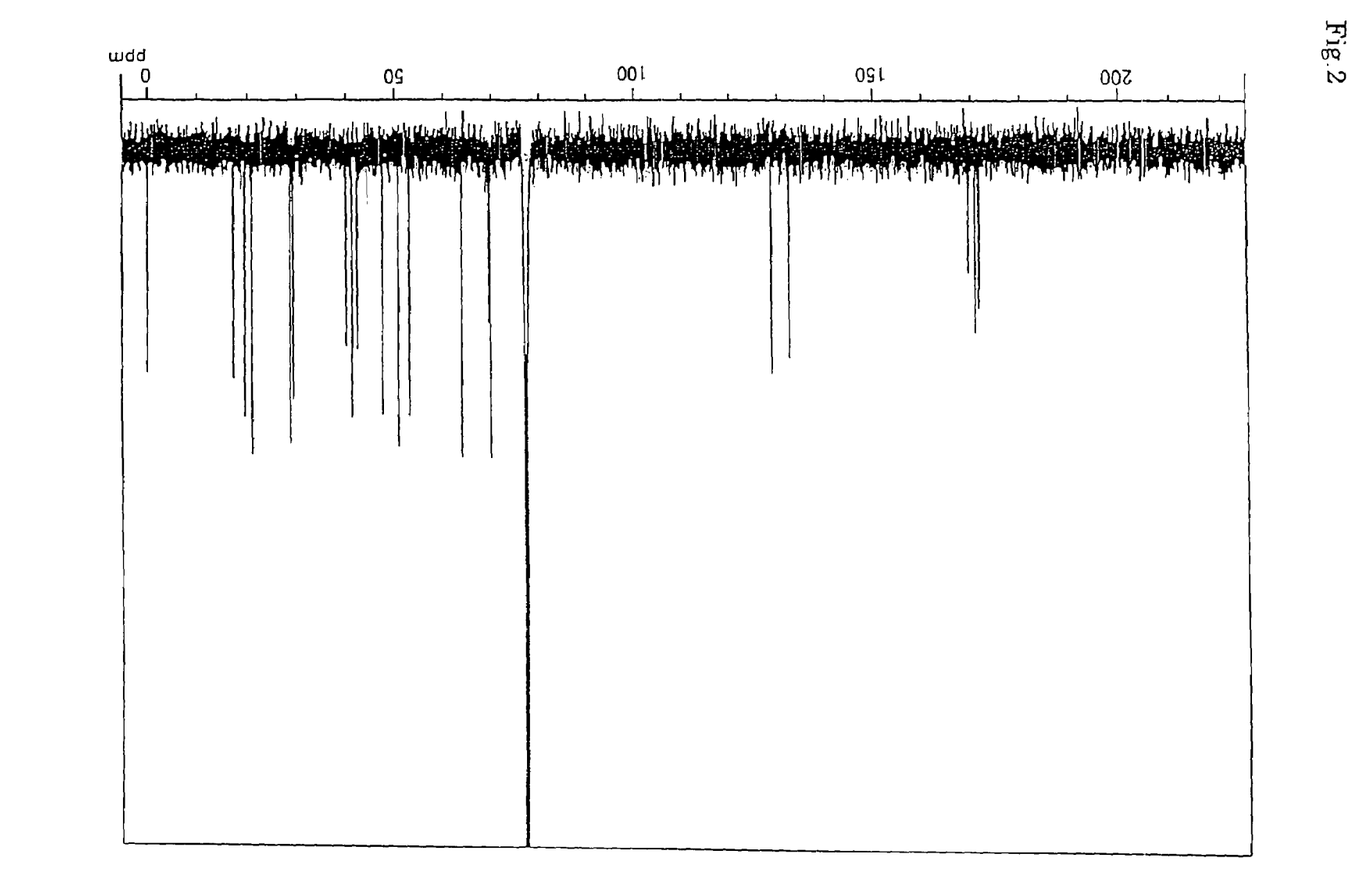
FIG. 2 shows the $^{13}$C-NMR spectrum of the compound Q.
Figure 3:
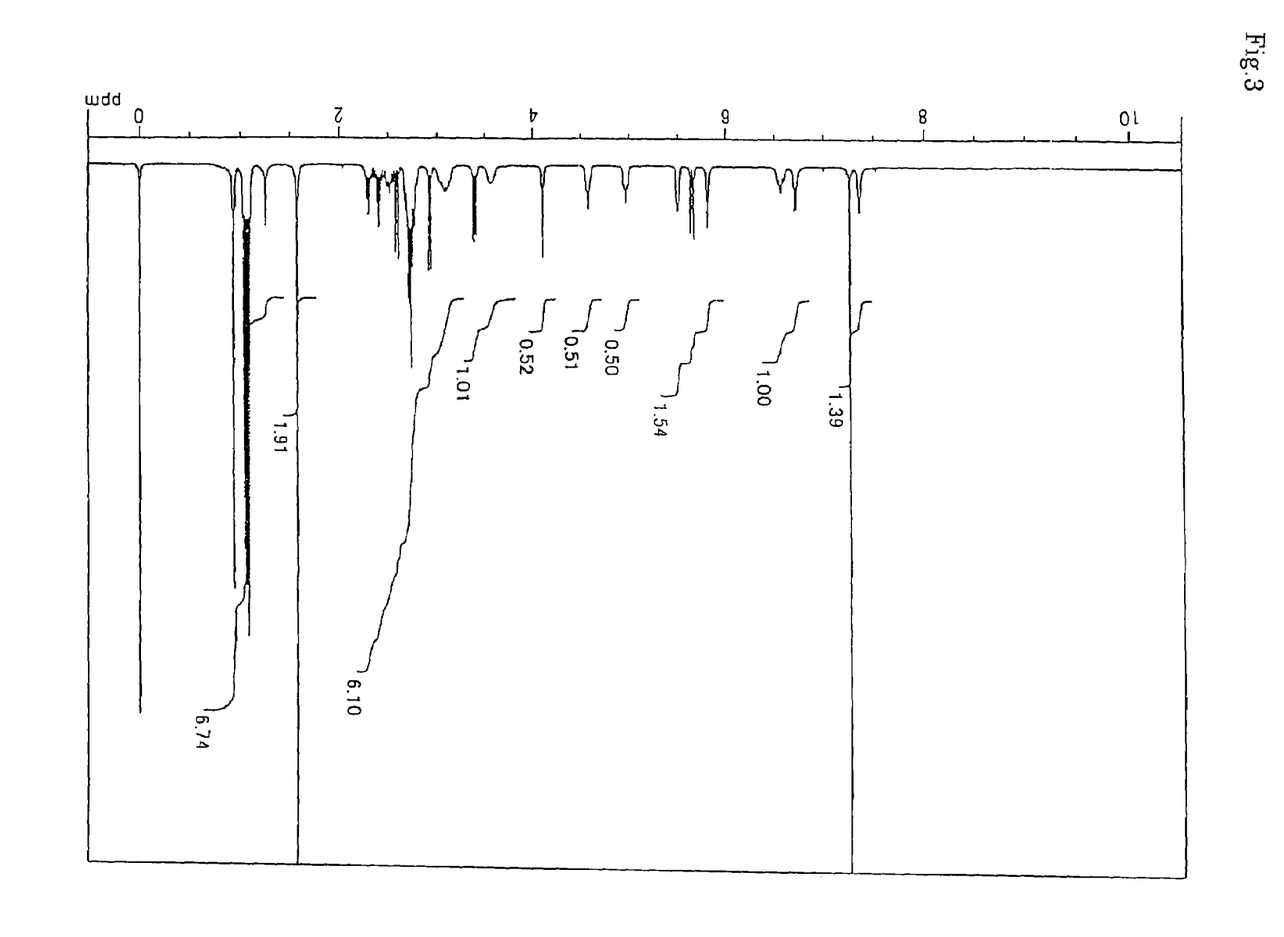
FIG. 3 shows the $^1$H-NMR spectrum of the compound R.
Figure 4:
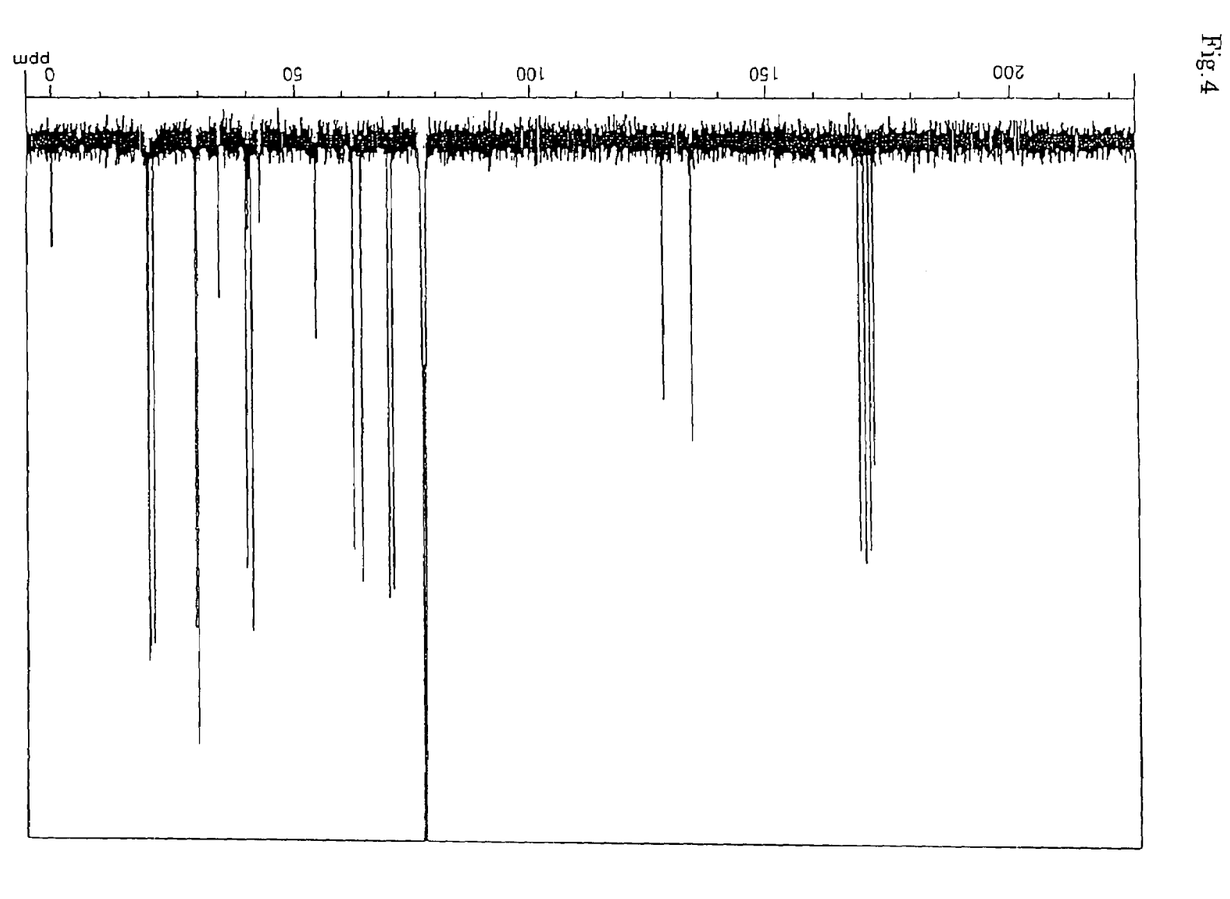
FIG. 4 shows the $^{13}$C-NMR spectrum of the compound R.

The physicochemical properties of the compounds Q and R obtained in the foregoing Examples are shown in the following Table 1. Additionally, NMR chart papers are shown in FIGS. 1 to 4 described below.

TABLE 1

| | Compound Q | Compound R |
|---|---|---|
| Color and form | White powder | White powder |
| Optical rotation $[\alpha]^{25}_D$ | −349.3° (c 0.05, MeOH) | −65.3° (c 0.20, MeOH) |
| Molecular formula | $C_{20}H_{31}N_3O_6S_3$ | $C_{22}H_{35}N_3O_6S_2$ |
| High resolution mass spectrometry (FAB) | | |
| Experimental value | 506.1442 (M + H)⁺ | 502.2059 (M + H)⁺ |
| Calculated value | 506.1453 | 502.2046 |
| Ultraviolet-visible absorption spectrum $\lambda_{max}^{MeOH}$ nm (ε) | 265 (1600) | End absorption |
| Infrared absorption spectrum $\nu_{max}$ (KBr) cm⁻¹ | 3320, 2960, 2930, 1740, 1660, 1550, 1510, 1430, 1320, 1260, 1160, 1040 | 3380, 3330, 2960, 2930, 2880, 1740, 1670, 1540, 1520, 1430, 1360, 1300, 1270, 1160 |

From the foregoing physicochemical properties, the chemical structural formulae of the compounds Q and R were determined as follows.

Compound Q

Compound R

Additionally, by reducing the compound R, the depsipeptide compound represented by the following formula (IIa) can be easily produced. The depsipeptide compound represented by the following formula (IIa) is considered to have an HDAC inhibitory activity in the same way as the compounds Q and R do (see JP-A-2001-354694).

(IIa)

INDUSTRIAL APPLICABILITY

It was confirmed that the compound of the present invention has an HDAC inhibitory activity and shows an inhibitory activity of cell proliferation against human cancer cells as shown in the Experimental Examples described below. Therefore, the compound of the present invention is effective for treatment and improvement of diseases and pathogenic conditions related to acetylation of histone, in particular, tumor or cell proliferative diseases, and further progressive neurodegenerative diseases such as Huntington's disease. Examples of the cell proliferation disease include, for example, infectious diseases, autoimmune diseases and dermatologic diseases. Particularly, since the compound of the present invention has a good inhibitory activity of cell proliferation against human cancer cells, it is useful as an antitumor agent. Furthermore, the compound of the present invention is also useful in promoting efficiency in the vector introduction in gene therapy and enhancing the expression of an introduced gene.

The usefulness of the compound of the present invention was confirmed by the following experiments.

EXPERIMENTAL EXAMPLE 1

Study for HDAC Inhibition (1) Partial Purification of HDAC

The nuclei isolated from human leukemia K562 cells were extracted according to the method of Yoshida et al. (Yoshida, M. et al., *J. Biol. Chem.*, 265, 17174–17179, 1990). Then, partial purification of HDAC was performed for the extracted solution with a NaCl concentration gradient from 0 to 0.5 M using a Q Sepharose FF column (Pharmacia Co.; 17-0510-01). Subsequently, dialysis was performed with HDA buffer [15 mM potassium phosphate (pH 7.5), 5% glycerol and 0.2 mM EDTA].

(2) Assay for HDAC Inhibitory Activity

The biotinylated [³H] acetyl-histone H4 peptide (aa 14-21: Biotin-Gly-Ala-[³H-acetyl]Lys-Arg-His-Arg-[³H-acetyl]Lys-Val-amide (SEQ ID NO:1)(Amersham Pharmacia Biotech Co.), hereinafter abbreviated as [³H] acetyl-histone) synthesized in accordance with Nare, B. et al., *Anal. Biochem.* 267, 390–396, 1999 was used as a substrate for HDAC inhibitory assay.

[³H] acetyl-histones were diluted to be a concentration of 37 μM with HDA buffer containing 60 μM dithiothreitol (DTT). After mixing 25 μl of the diluted [$^3$H] acetyl-histones and 25 μl of the HDAC fraction purified and dialyzed in (1), reaction at room temperature for 2 hours was carried out. In order to stop the reaction, 50 μl of 1 M hydrochloric acid was added thereto and further 800 μl of ethyl acetate was added. Mixing and centrifugation were carried out, 400 μl of the ethyl acetate layer was collected into a scintillator vial and 5 ml of scintillator was added. The radioactivity of the released [$^3$H] acetic acid was measured with a liquid scintillation counter.

The inhibitory activity of the medicament against HDAC was examined by adding 2 μl of the medicament dissolved and diluted with dimethylsulfoxide (DMSO) before the mixing of the substrate and the enzyme, and by performing the foregoing assay.

The compounds Q and R of the present invention showed a good HDAC inhibitory activity and showed an inhibitory activity of HDAC enzyme of 50% or more at the concentration of 10 nM, respectively.

EXPERIMENTAL EXAMPLE 2

Study for Inhibition of Cell Proliferation Against Human Cancer Cells

Human colon cancer WiDr cells or human leukemia K562 cells were inoculated into a 96-well test plate at a density of $5\times10^3$ cell/well and cultured at 37° C. in a 0.5% $CO_2$ incubator. Eighteen hours after the inoculation, the solvent (DMSO) diluted with the medium and various concentrations of the compound Q or R were added, and followed by further culture at 37° C. in a 0.5% $CO_2$ incubator for 72 hours. After the culturing, the proliferation of cells was measured with Alamar Blue (BIOSOURCE Co.). The measurement values for the conditions in which 0.1% DMSO and cells had been added, and 0.1% DMSO had been added and cells had not been added were assigned to be 0% inhibition and 100% inhibition, respectively, and the proliferation inhibition rate for each concentration of the compounds was obtained, then the concentration of inhibiting proliferation by 50% (IC50 value) was calculated by logistic regression. As a result, the IC50 values of inhibition of cell proliferation of the compound Q against WiDr cells and K562 cells were 3.0 nM and 1.4 nM, respectively, and the IC50 values of inhibition of cell proliferation of the compound R against WiDr cells and K562 cells were 0.9 nM and 0.6 nM, respectively, which shows that both compounds had a good inhibitory activity of cell proliferation.

EXPERIMENTAL EXAMPLE 3

Effect on Inducing Histone Acetylation Against Human Cancer Cells

After inoculating K562 cells into a 35 mm dish at a density of $1.5\times10^6$ cell/dish, the solvent (DMSO) and various concentrations (0.3 to 30 nM) of the compound Q or R were added and cultured at 37° C. in a 0.5% $CO_2$ incubator for 24 hours. Extraction of the histone protein was performed by the following method. To the cell precipitate collected by centrifugation, TEN buffer (10 mM Tris HCl (pH 8.0), 1 mM EDTA, 1% NP-40, 1 tablet/10 mL Complete mini (Roche Co.)) was added, stood on the ice for 10 minutes, and the supernatant was collected by centrifugation. The supernatant was mixed well with an equal amount of 0.4 M sulfuric acid, and stood on ice for 1 hour. The supernatant portion was collected by centrifugation, mixed with 5 times amount of acetone and stood at -20° C. for 12 hours or more. The precipitate was collected by centrifugation, washed once with acetone, and then the precipitate was dried. The precipitate was dissolved in distilled water, which was made to be histone protein, the protein concentration was determined by the Bradford method. The amounts of histone proteins were adjusted to be an equal amount, and SDS-PAGE and Western blotting were performed in accordance with the usual method. For the primary antibody, an anti-acetylated histone H3 antibody (UPSTATE biotechnology Co.), for the secondary antibody, an HRP labeled anti-rabbit antibody (Amersham Pharmacia Biotech Co.) were used, and luminescence was detected by ECL (Amersham Pharmacia Biotech Co.). As a result, with regard to the samples treated with the compound Q or R, significant and dose-dependent bands of acetylated histone H3 were detected in comparison with the sample treated with solvent. Accordingly, it was confirmed that the compounds-Q and R of the present invention inhibit HDAC and promote histone acetylation also in K562 cells.

Sequence Table Free Text

The explanation of "Artificial Sequence" is described in the numerical index <223> of the following Sequence Listings. Specifically, in the amino acid sequence represented by the sequence of SEQ ID NO:1 in the Sequence Listings, both the third and seventh amino acids from the N-terminal: Xaa, show $N^6$-[$^3H_1$]acetyllysine, which is an artificially synthesized peptide.

What is claimed is:

1. An isolated depsipeptide compound of formula (I) or (II), or a pharmaceutically acceptable salt thereof:

(I)

(II)

2. An isomer of a depsipeptide compound having the planar structural formula represented by the formula (I) described in claim 1 and an optical rotation $[\alpha]^{25}_D$ of −349.3 degree (c 0.05, methanol solvent) or an isomer of a depsipeptide compound having the planar structural formula represented by the formula (II) described in claim 1 and an optical rotation $[\alpha]^{25}_D$ of −65.3 degree (c 0.20, methanol solvent), or a pharmaceutically acceptable salt thereof.

3. A pharmaceutical composition comprising the depsipeptide compound or the pharmaceutically acceptable salt thereof according to claim 1 and a pharmaceutically acceptable carrier.

4. A method for treating cancer, which comprises administering an effective amount of the depsipeptide compound or the pharmaceutically acceptable salt thereof according to claim 1 to a patient suffering from cancer.

* * * * *

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: biotinylated acetyl-histone H4 peptide
<220> FEATURE:
<221> NAME/KEY: MOD_RES
<222> LOCATION: (3)..(3)
<223> OTHER INFORMATION: N6-[3H1]acetyllysine
<220> FEATURE:
<221> NAME/KEY: MOD_RES
<222> LOCATION: (7)..(7)
```

```
<223> OTHER INFORMATION: N6-[3H1]acetyllysine

<400> SEQUENCE: 1

Gly Ala Xaa Arg His Arg Xaa Val
1               5
```